(12) United States Patent
Woods et al.

(10) Patent No.: US 11,413,365 B2
(45) Date of Patent: Aug. 16, 2022

(54) DISINFECTION SYSTEM FOR MASS TRANSIT VEHICLES

(71) Applicant: CleanSpray USA LLC, Lewisville, TX (US)

(72) Inventors: Anthony R. Woods, Lewisville, TX (US); Cory A. Strange, Lewisville, TX (US)

(73) Assignee: CLEANSPRAY USA LLC, Lewisville, TX (US)

( * ) Notice: Subject to any disclaimer, the term of this patent is extended or adjusted under 35 U.S.C. 154(b) by 0 days.

(21) Appl. No.: 17/509,969

(22) Filed: Oct. 25, 2021

(65) Prior Publication Data

US 2022/0125973 A1 Apr. 28, 2022

Related U.S. Application Data

(60) Provisional application No. 63/105,339, filed on Oct. 25, 2020.

(51) Int. Cl.
*A61L 9/00* (2006.01)
*A61L 2/00* (2006.01)
*A61L 2/22* (2006.01)
*B60S 1/64* (2006.01)
*A61L 2/24* (2006.01)

(52) U.S. Cl.
CPC ........ *A61L 2/22* (2013.01); *A61L 2/24* (2013.01); *B60S 1/64* (2013.01); *A61L 2202/14* (2013.01); *A61L 2202/15* (2013.01); *A61L 2202/25* (2013.01)

(58) Field of Classification Search
CPC .......... A61L 2/0094; A61L 9/015; A61L 2/20; A61L 9/14; A61L 2/24; A61L 2202/11; A61L 2/26; A61L 2202/15; A61L 2202/16; A61L 2202/25
USPC ................... 422/292, 300, 305–306
See application file for complete search history.

(56) References Cited

U.S. PATENT DOCUMENTS

| | | | | |
|---|---|---|---|---|
| 2,348,574 A | * | 5/1944 | Ross | A61L 2/06 422/307 |
| 3,301,488 A | * | 1/1967 | Edward | B05B 7/0846 239/752 |
| 2020/0306399 A1 | * | 10/2020 | Markesbery | A01N 65/22 |

* cited by examiner

*Primary Examiner* — Monzer R Chorbaji (57) ABSTRACT

A system for disinfecting a mass transit vehicle includes a storage tank for storing a disinfection solution. A plurality of nozzles are installed in the interior of the mass transit vehicle. The plurality of nozzles projecting droplets of the disinfection solution into the interior of the mass transit vehicle when the system is activated. A pump pumps the disinfection solution from the storage tank to the plurality of nozzles on the interior of the mass transit vehicle. A control switch initiates operation of the system. A system indicator indicates an operational status of the system. A controller controls the operation of the pump responsive to an input from the control switch. Responsive to actuation of the control switch to a first position, the controller actuates the system indicator for a first predetermined period of time and actuates the pump to pump the disinfection solution from the storage tank to the plurality of nozzles on the interior of the mass transit vehicle for a second predetermined period of time after expiration of the first predetermined period of time.

19 Claims, 11 Drawing Sheets

DISINFECTION SYSTEM FOR MASS TRANSIT VEHICLES

CROSS-REFERENCE TO RELATED APPLICATIONS

This application claims benefit of U.S. Provisional Application No. 63/105,339, filed Oct. 25, 2020, entitled DISINFECTION SYSTEM, the specification of which is incorporated by reference herein in its entirety.

TECHNICAL FIELD

The present disclosure generally relates to disinfection and/or sterilization, and more particularly to disinfection systems for areas of public transportation vehicles.

BACKGROUND

Disinfection and/or sterilization can be very important in preventing illnesses and especially once an outbreak arises. However, in large vehicles, such as mass transportation and school busses, it can be difficult to easily disinfect and/or sterilize these environments. It often requires cleaning personnel to manually perform the disinfection and/or sterilization, which can be prone to errors or incompleteness. Manual cleaning can be costly in terms of labor and continued spread of disease if performed incorrectly.

SUMMARY

The present invention, as disclosed and described herein, in one aspect thereof comprise a system for disinfecting a mass transit vehicle including a storage tank for storing a disinfection solution. A plurality of nozzles are installed in the interior of the mass transit vehicle. The plurality of nozzles projecting droplets of the disinfection solution into the interior of the mass transit vehicle when the system is activated. A pump pumps the disinfection solution from the storage tank to the plurality of nozzles on the interior of the mass transit vehicle. A control switch initiates operation of the system. A system indicator indicates an operational status of the system. A controller controls the operation of the pump responsive to an input from the control switch. Responsive to actuation of the control switch to a first position, the controller actuates the system indicator for a first predetermined period of time and actuates the pump to pump the disinfection solution from the storage tank to the plurality of nozzles on the interior of the mass transit vehicle for a second predetermined period of time after expiration of the first predetermined period of time.

BRIEF DESCRIPTION OF THE DRAWINGS

For a more complete understanding, reference is now made to the following description taken in conjunction with the accompanying Drawings in which.

DETAILED DESCRIPTION

Referring now to the drawings, wherein like reference numbers are used herein to designate like elements throughout, the various views and embodiments of a disinfection system for mass transit vehicles are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Embodiments of the present disclosure may provide a disinfection system that may include a fixed-mounted device that may sterilize and/or disinfect large areas within a mass transit vehicle such as a bus, school bus, shuttle, train, subway, airplane, etc. Large areas may include, but are not limited to, rooms and the interiors of large, mass transit vehicles. A botanical component disinfectant certified to kill various contaminants, including human coronavirus, may be used to sterilize and/or disinfect the large areas. While the description references the use of a botanical disinfectant, any disinfectant/sterilization agent may be utilized that does not risk the health and well being of passengers of the vehicle.

A disinfection system according to embodiments of the present disclosure may include a fixed-mounted device, a botanical component that comprises the generated fog/spray from the system, a storage unit for the botanical component, a series of hoses and nozzles, and a controller that may be used to actuate disinfection and/or sterilization of the large areas within a mass transit vehicle. Additionally, a timer can be used to schedule disinfection and/or sterilization of the areas on a regular schedule. The botanical component should be approved and certified for disinfection purposes. The series of hoses may distribute the botanical component to the series of nozzles. It should be appreciated that the series of nozzles may be capable of delivering specified quantities that may be tailored to the size of the area being sterilized and/or disinfected. The controller initiates the release of the botanical compound responsive to a user actuation. The timer may establish an interval for scheduling release of the botanical component.

Figure 1:
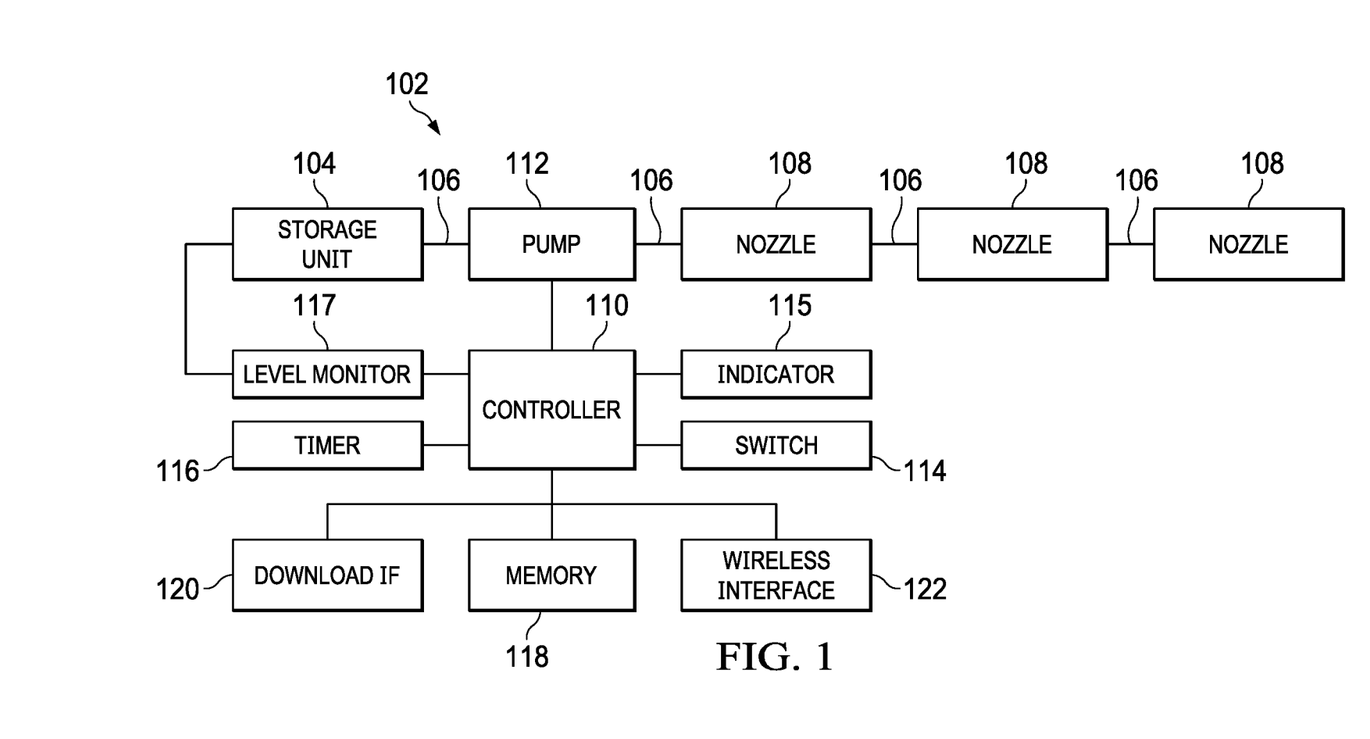
FIG. 1 illustrates a block level diagram of a disinfection system.

FIG. 1 depicts disinfection system 102 according to an embodiment of the present disclosure. Storage unit 104 houses botanical component from which the generated fog/mist/spray is created. It should be appreciated that storage unit 104 may have a variable size depending on the amount (i.e., number of gallons) of botanical component to be housed within storage unit 104. The variability of size also may depend on the size of the area being sterilized and/or disinfected. One or more hoses 106 may be attached to storage unit 104 to extract botanical component from storage unit 104. Controller 110 is used for controlling operation of a pump 112. The pump 112 pumps the botanical component from the storage unit 104 to multiple nozzles 108 for diffusion into the interior of the mass transit vehicle. The controller 110 actuates the pump 112 to disperse the botanical component responsive to actuation of a switch 114. The switch may comprise in one embodiment a solid-state rocker switch that would function well in rough and high vibration environments. The pump 112 and other electrical components of the system operate using 12 V power in order to not impede existing electrical system functions. A timer 116 may also actuate the controller 110 to schedule disinfection and/or sterilization of the large areas within a mass transit vehicle. A level monitor 117 monitors the fluid level within the storage unit 104. Responsive to detection of the level of fluid dropping to a predetermined level by the level monitor 117, the controller 110 causes the actuation of an indicator 119 (LED, audible alarm, etc.) to notify an operator of a need to refill the storage unit 104. In one embodiment, the indicator 119 may comprise a green LED to indicate all system components are ready and working and a red LED to indicate that the system needs service. The operation of the level monitor 117 and controller 110 will be more fully described with respect to FIG. 11 hereinbelow.

The controller 110 continuously monitors the system and provides a number of warning functions and system control operations. If the level monitor 117 detects an empty storage unit 104, the system can provide a warning/error indication using the indicator 119. The controller 110 may also monitor the pump 112 operation to detect if the pump motor has lost prime and generate a warning indication if this occurs. The controller 110 can shut down the system if a failure mode is detected to provide over current and over temperature protection when these conditions are detected in the pump motor. The controller 110 may also generate error indications if it determines that the pump motor is shorted or disconnected or if a sensor is malfunctioning or missing.

A memory 118 may also be associated with the controller 110 to store information related to each actuation of the system 102 to disinfect/sanitize a mass transit vehicle. The memory 118 can store an audit record of when a vehicle was sanitized to be used to provide evidence of the application of the botanical component by the system to a vehicle interior. The information within the memory 118 can be downloaded either directly from memory or through the controller 110 using a download interface 120. The download interface 120 may provide a wired or wireless (RF, Bluetooth, WiFi, etc.) connection to enable the audit data from the memory to be downloaded to an external party. The controller 110 can also actuate the pump 112 responsive to commands received at the controller over a wireless interface 122 that provides wireless communications between the controller 110 and an external command source for controlling the system. The wireless interface and/or the download interface 120 may provide Bluetooth connectivity to enable a user to configure system settings (spray time, system start delay, etc.), to view system audit logs, technicians to monitor system operations and parameters for maintenance and troubleshooting purposes through the controller 110.

The one or more hoses 106 may deliver botanical component to one or more additional hoses 106 that may be attached to one or more nozzles 108 that deploy botanical component to the areas to be sterilized and/or disinfected. A botanical component comprise a plant based liquid material that may be provided from the nozzles 108. While FIG. 1 depicts three nozzles 108, it should be appreciated that more or fewer nozzles may be utilized within disinfection system 102 without departing from the present disclosure. The number and/or size of nozzles 108 may depend on the size of the area being sterilized and/or disinfected. Misting/fogging nozzles 108 may be used that may create a finely atomized spray having uniform droplet size, consistent spray angles, and relatively low pressures. There may be embodiments of the present disclosure where different pressures may be needed, and accordingly, nozzles 108 may provide variable water pressures as needed.

The controller 110 and other system components can in an alternative embodiment have a CAN bus connection to the vehicle OBDII and computer system. This would enable the system to be integrated into vehicle system control. The controller 110 may further provide an operation interlock function that can prevent the system from starting a disinfection operation while the vehicle is in gear or motion to prevent inadvertent spraying of passengers or drivers. The controller 110 can also be configured to prevent the system from starting after the system timer is off. This is the same timer that turns vehicle lights off to prevent the lights from draining the battery dead. By interconnection with the CAN bus, the system can provide a number of other functionalities including enabling illumination of indicators on a dash cluster, supporting multiple keypads mounted on the interior and exterior of the vehicle, monitoring vehicle status (open doors, etc.) while the system is in operation, and enabling the system to flash vehicle marker lights while spraying.

The system may also provide various cold weather functionalities such as flushing liquid from the nozzles to prevent damage in freezing temperatures when colder weather is detected below a predetermined temperature. The system may also include insulated storage unit 104 with an integrated heating pad to keep the storage unit from freezing in cold temperatures.

Figure 2:
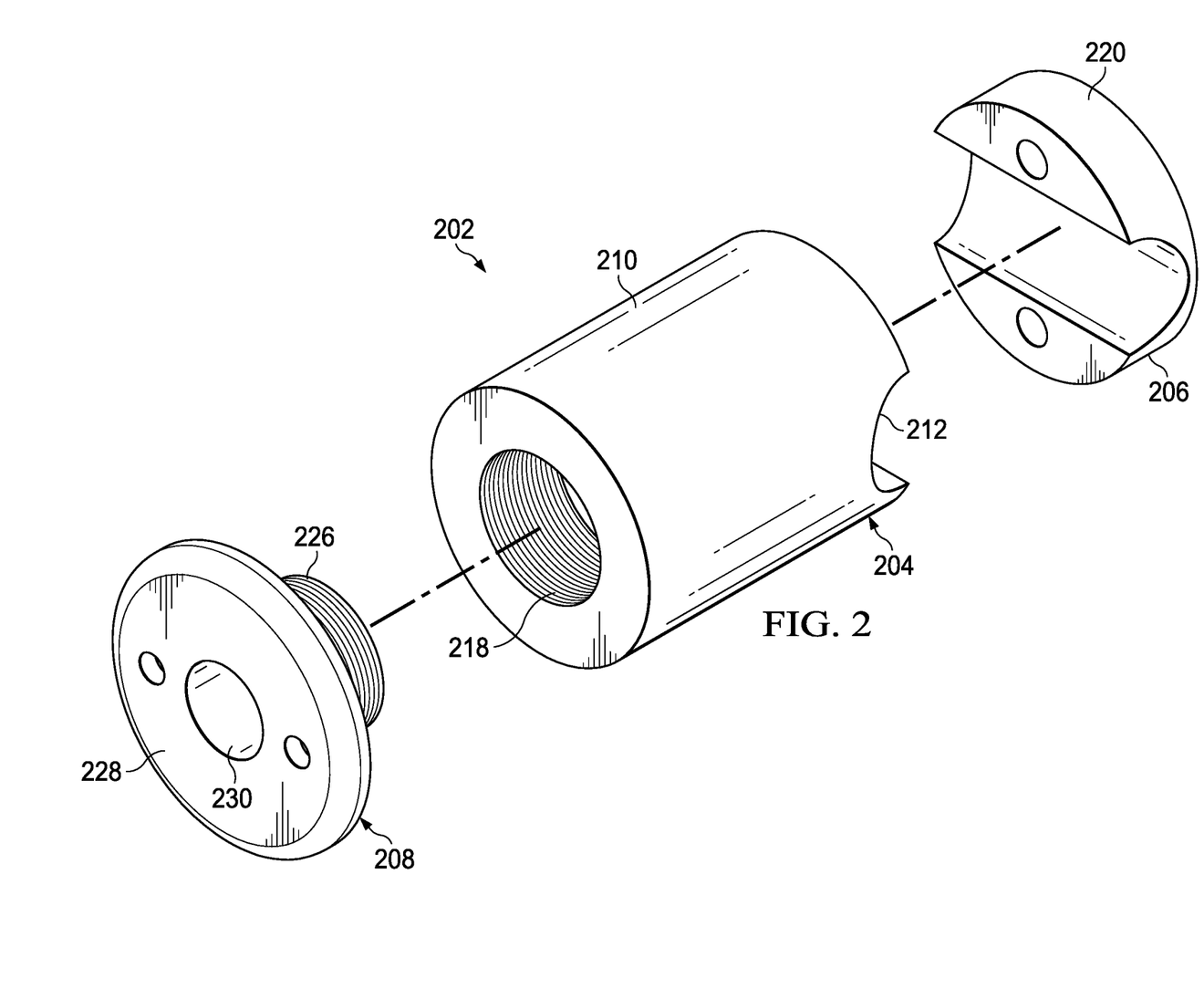
FIG. 2 illustrates a view of the holder base assembly of the nozzle assembly.
Figure 3:
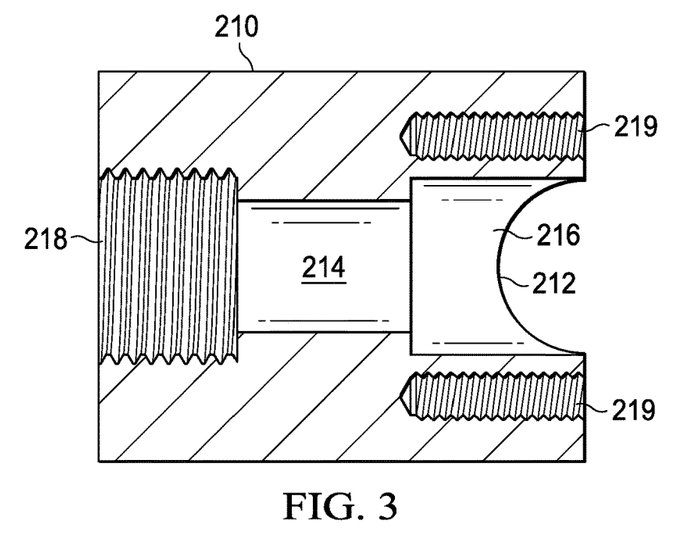
FIG. 3 illustrates a cross-sectional view of the holder base.

With respect to the nozzles 108, the configuration of the nozzles enable them to be installed within the existing infrastructure of a mass transit vehicle. By running the tubing connecting the nozzles 108 with the storage unit 104 behind existing paneling and using structures such as the light bars within vehicles, the nozzles can be installed within the mass transit vehicles in a relatively easy fashion. Referring now to FIGS. 2-7, there is illustrated an embodiment of the nozzle assembly that provides for ease of installation within existing mass transit vehicle structures. Referring now to FIG. 2, there is illustrated a perspective view the nozzle holder assembly 202. The nozzle holder assembly 202 consist of the holder base 204, holder base cap 206 and holder trim ring 208. The holder base 204 as further shown in FIG. 3 in a cross-sectional view comprises a cylindrical body 210. The cylindrical body 210 has a circular notch 212 defined across a central axis of the cylindrical body for clamping a T-portion of the spray nozzle as will be more fully described herein below. The interior of the cylindrical body 210 defines a cylindrical opening 214 through which a spray nozzle assembly may pass. The interior of the cylindrical body 210 further defines a bored opening 216 into which the T-portion of the spray nozzle assembly may be inserted when clamped into the holder base 204. The cylindrical body 210 also defines a threaded opening 218 into which the holder trim ring 208 may be threaded. The interior walls of the opening 218 are threaded to engage threads on the holder trim ring 208 as will be more fully described herein below. The cylindrical body 210 further defines a pair of threaded screw holes 219 into which screws may be threaded in order to secure the holder base cap 206 to the holder base 204.

Figure 4:
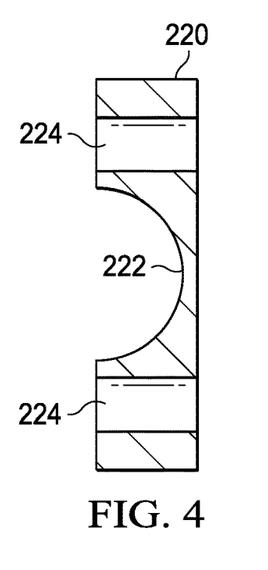
FIG. 4 illustrates a cross-sectional view of the holder base cap.

The holder base cap 206 as shown also in cross-section in FIG. 4 comprises a circular disk cylinder 220 having a same diameter as the holder base 204. The holder base cap 206 also defines a circular notch 222 that aligns with circular notch 212 of the holder base 204 such that a T-portion of the spray nozzle assembly may be clamped therein as will be more fully described herein below. The holder base cap 206 further defines a pair of threaded screw holes 224 which align with the threaded screw holes 219 of the holder base 204.

Figure 5:
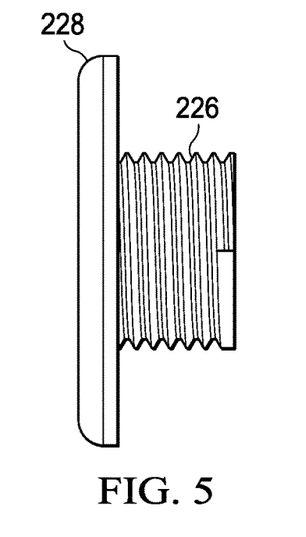
FIG. 5 illustrates a side view of the holder base trim ring.

The holder trim ring 208 includes a threaded circular cylinder 226 that threadedly engages the interior of threaded opening 218 of the holder base 204. Sitting at one end of the threaded circular cylinder 226 is a circular disk cap 228 that is perpendicular to the central axis of the threaded circular cylinder 226. The holder trim ring 208 further defines a cylindrical opening 230 along the central axis of the threaded circular cylinder 226. Through this opening 230, the nozzle may be inserted and dispense the botanical component.

Figure 6:
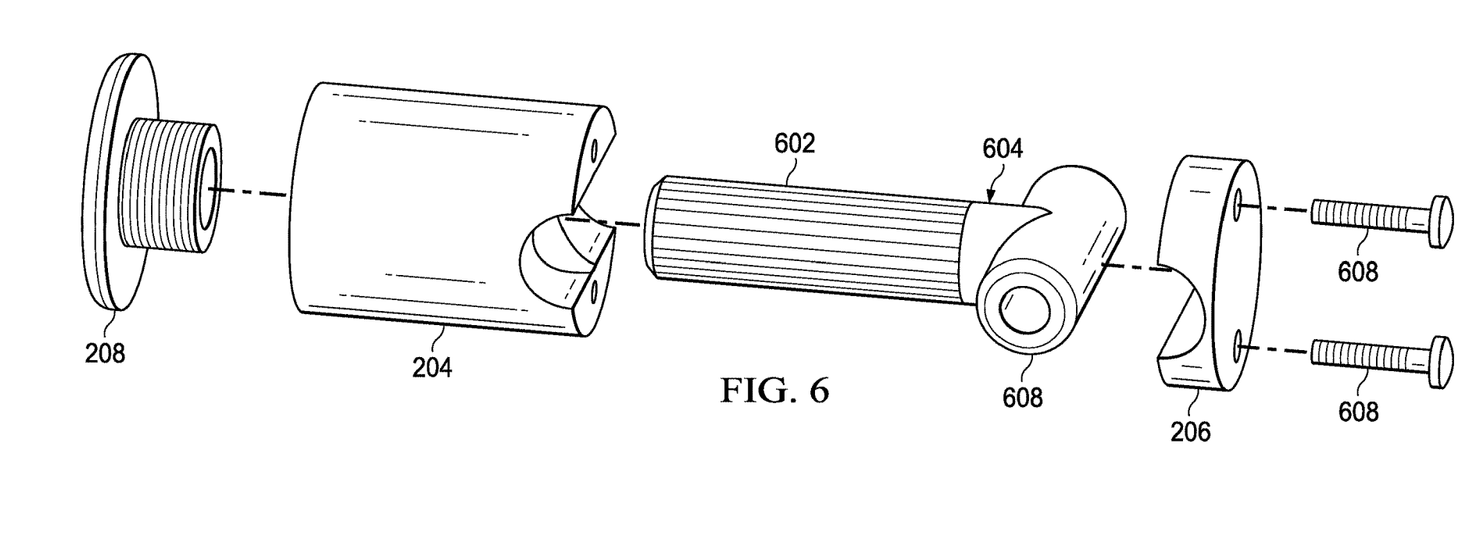
FIG. 6 illustrates an exploded perspective view of the nozzle assembly.

Referring now to FIG. 6, there is more particularly illustrated the manner in which the complete nozzle assembly is assembled. A nozzle 602 defining a channel therein is threaded on to a base of a T-portion 604. The T-portion 604 includes the base which threadedly engages a nozzle 602. The cross piece of the T-portion provides a pass-through opening for interconnecting the nozzle assemblies with hoses 106 that interconnect nozzles or connects a nozzle to the pump 112. The nozzle 602 is inserted through the cylindrical opening of the holder base 204. The cross piece is 608 will engage with the circular notch 212 of the base holder 204. The nozzle 602 and T-portion 604 assembly is secured to the holder base 204 by placing the holder base cap 206 such that the circular notch 222 of the holder base cap engages the cross piece 608 of the nozzle assembly. The holder base cap 206 is secured to the holder base 204 using a pair of screws 608 that threadedly engage the holes 224 of the holder base cap 206 and the holes 219 of the holder base cap 204. The holder trim ring 208 is inserted into the threaded opening 218 of the holder base 204 and screwed tight to secure the assembly to a panel between the front face of the holder base 204 and the back face of the holder trim ring 208. In this manner, the nozzle assembly may be secured to a panel of an interior structure of a mass transit vehicle as will be more fully described in FIG. 7.

The nozzle assembly once assembled would in one embodiment provide up to 120 degrees of coverage from each nozzle. The coverage area can of course be altered to a greater or lesser number of degrees in order to provide coverage for a particular area of a mass transit vehicle. The nozzle assembly may be constructed in one embodiment of aircraft aluminum to provide for a long lifespan and rugged durability.

The nozzles 602 may also comprise an air atomizing nozzle. The nozzles 602 would provide ultra-small particle sizes to create a fast-drying fog providing superior surface coating in an area. In one embodiment, the low-pressure system requirements would have compressed air requirement of 20-45 PSI and a liquid disinfecting requirement of 10-30 PSI. The nozzles 602 may also be interchangeable to provide directional or wide-angle patterns (up to 120 degrees) within the mass transit vehicle. The system may also support integration with the mass transit vehicles compressed air system or can be retrofitted with a stand-alone system. The nozzles may be constructed of a variety of materials including stainless steel, plastic using 3D printing, etc.

Figure 7:
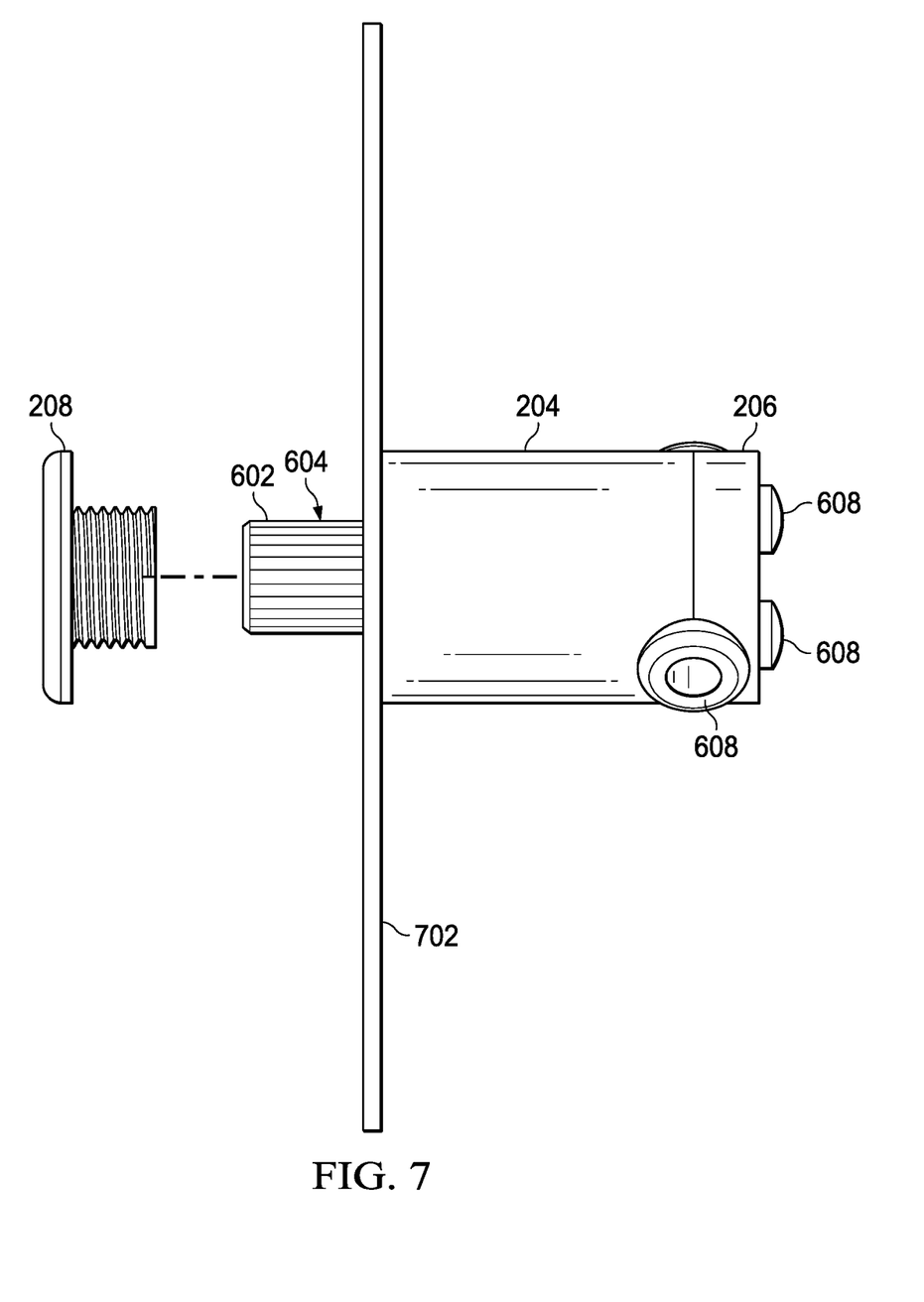
FIG. 7 illustrates a side view of the nozzle assembly installed on a structural panel.
Figure 8:
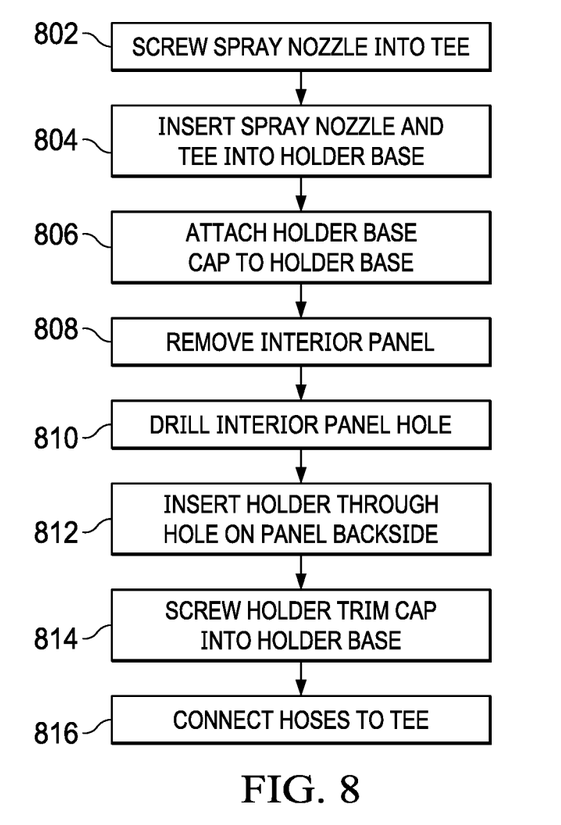
FIG. 8 illustrates a flow diagram of the process for installing the nozzle assembly.

Referring now to FIGS. 7 and 8, there is illustrated the manner in which a nozzle assembly may be installed on the interior of a mass transit vehicle using for example an interior panel or a light bar on a school bus. FIG. 7 provides an illustration of the manner in which the nozzle assembly is installed upon a panel 702 within a mass transit vehicle, and FIG. 8 is a flow diagram describing the process of assembling and installing the nozzle assembly. Initially, the spray nozzle 602 is screwed into the T-portion 604 at step 802. This spray nozzle assembly is inserted into the base holder 204 at step 804 with the spray nozzle 602 being inserted into the interior channel 214 of the base holder 604 and the T-portion resting in the circular notch 212 of the base holder 204. The holder base cap 206 is attached at step 806 to the holder base 204 using a pair of screws 608 threaded through aligned holes 224 and 219 of the holder base cap 206 and holder base 204. The T-portion crosspiece fits within the circular notch 222 of the holder base cap 206.

An installer will remove at step 808 an interior panel or housing 702 from the interior of the mass transit vehicle. A hole that is large enough to have the nozzle 602 inserted there through is drilled at step 810 into the panel or housing 702. The nozzle 602 extending from the holder housing 204 is inserted at step 812 through the hole from the backside of the panel 702 as illustrated generally in FIG. 7. The holder trim ring 208 is screwed on to the threaded portion of holder base 204. The holder trim ring 208 is screwed/tightened at step 814 such that the nozzle assembly is clamped in place with the front face of the holder base 204 pressing into the backside of the panel 702 and the back face of the holder trim ring 208 presses against the front side of the panel 702. In this manner, the nozzle assembly is secured to the panel 702. Hoses may then be inserted into the exposed openings of the T-portion 608 in order to provide the botanical component to and from the nozzle assembly and to be sprayed from the nozzle opening within the holder trim cap 208.

Figure 9A:
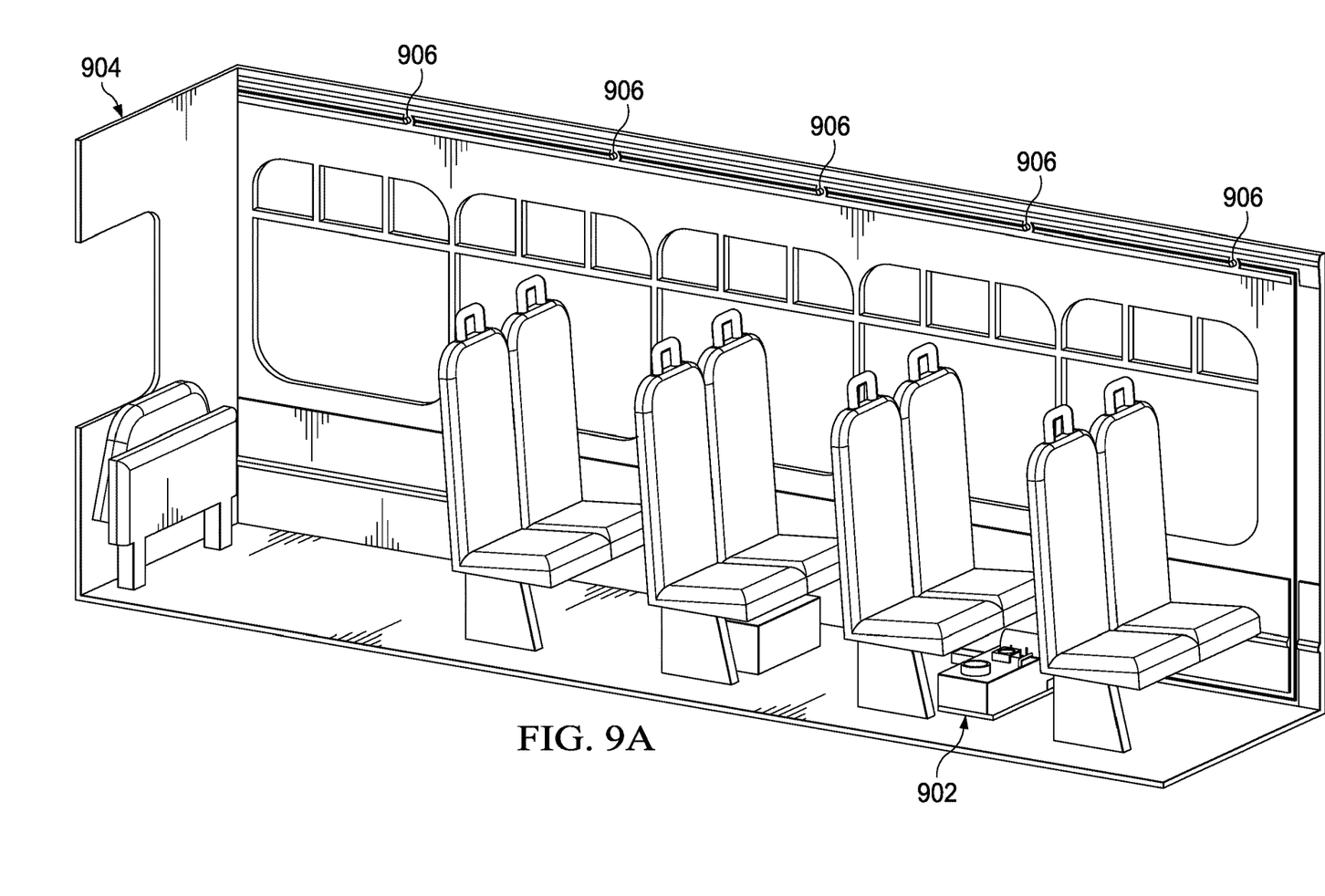
FIGS. 9A-9C illustrate the disinfection system installed upon a mass transit vehicle such as a school bus.
Figure 9B:
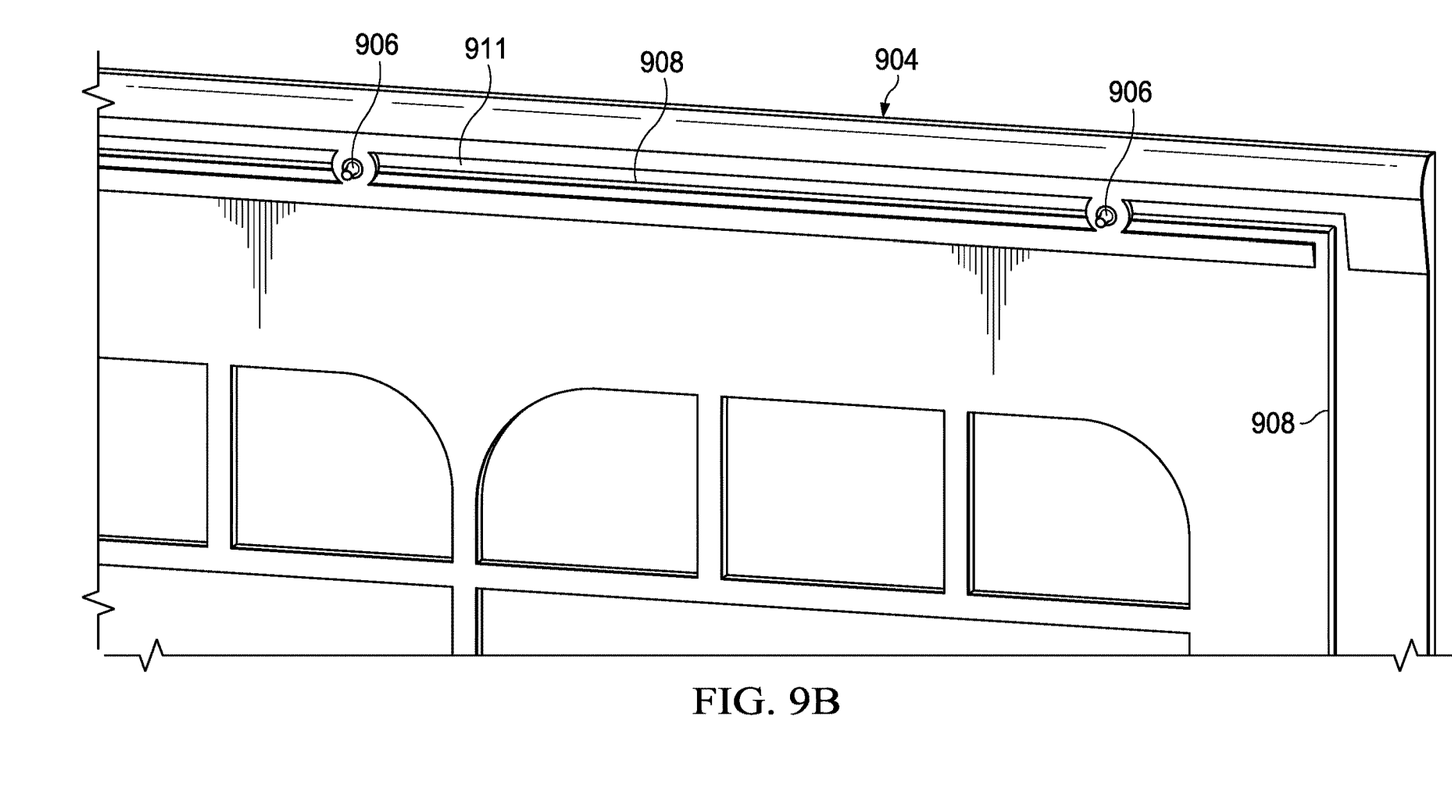
Figure 9C:
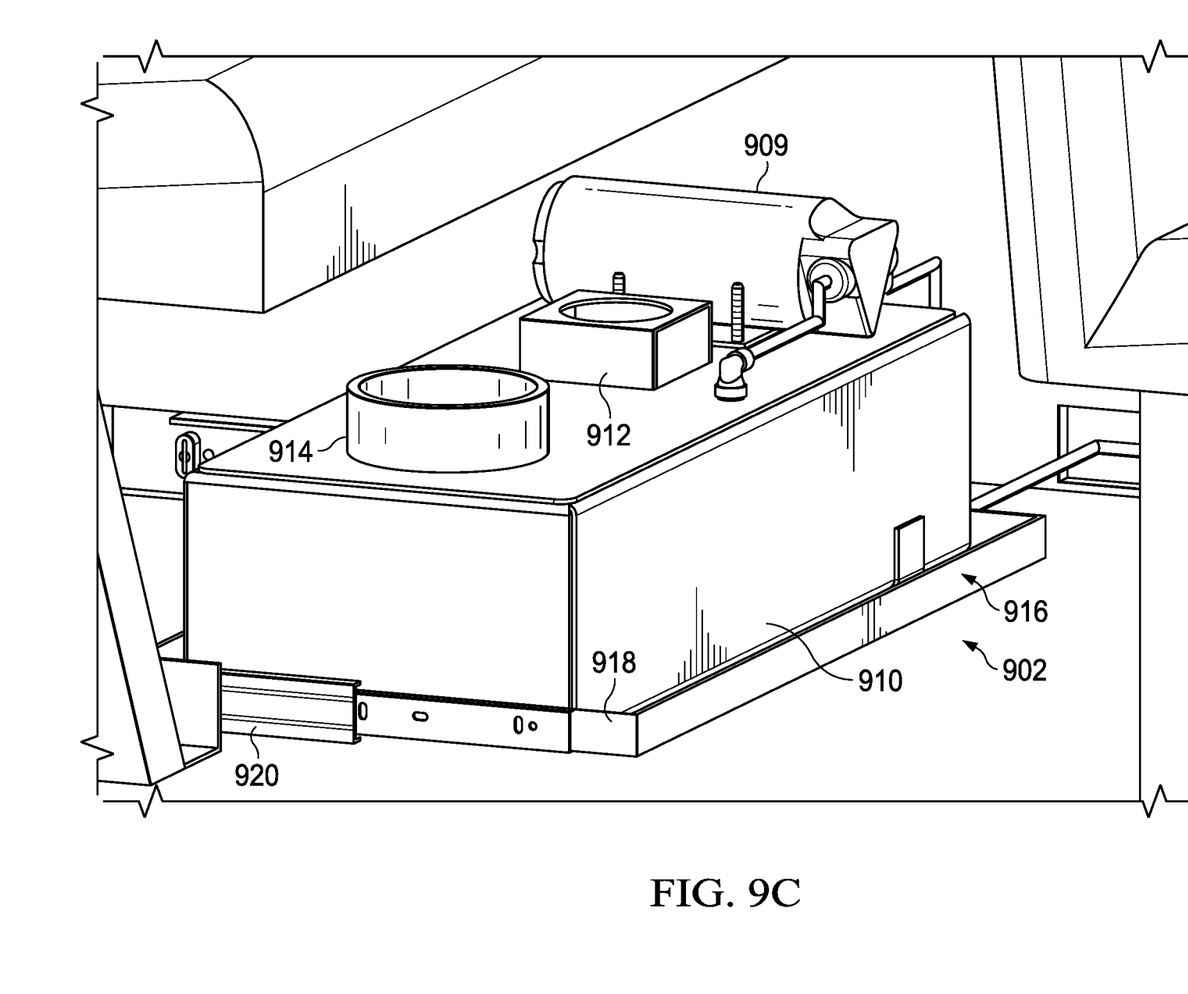

FIGS. 9A-9C depicts a disinfection system 902 deployed in large mass transit vehicle 904 according to an embodiment of the present disclosure. As depicted herein, large mass transit vehicle 904 is a school bus, but it should be appreciated that a large vehicle may include, but is not limited to, planes, trains, rails, school buses, shuttles, city buses, and other mass transit in embodiments of the present disclosure. Nozzles 906 may be deployed on each side of large mass transit vehicle 902 (i.e., nozzles on the driver side of large mass transit vehicle 904 and nozzles on the passenger side of large mass transit vehicle 902). In this embodiment of the present disclosure, there may be 8 joints with 16 nozzles 906 on the driver side of large mass transit vehicle 904 and 8 joints with 16 nozzles 906 on the passenger side of large mass transit vehicle 904. Each of the joints may be 4 feet apart; however, the joints may be larger or smaller without departing from the present disclosure. It also should be appreciated that there may be embodiments of the present disclosure where more or fewer nozzles 906 may be deployed on each side of large mass transit vehicle 904 depending on factors such as the size of large mass transit vehicle 904 and the concentration of botanical component to be deployed within large mass transit vehicle 904. In an embodiment of the present disclosure, nozzles 906 may be placed in 8 separate 4-foot pieces attached together with 2 nozzles per piece; however, other configurations may be used without departing from the present disclosure. The number and placement of the nozzles 906 can be customized based on the mass transit vehicle in which the system is being installed.

Nozzles 906 may be mounted in an extrusion joint, which may be standardized or customized, and they may be mounted one foot off each end. Again, while a distance for the mounting is described herein, it should be appreciated that the distance may be longer or shorter without departing from the present disclosure. Tubing 908 to deliver a botanical component to nozzles 906 may mount on one or more interior walls of large mass transit vehicle 904 and along the top light bar of large mass transit vehicle 904 in an embodiment of the present disclosure; however, other configurations for tubing 908 may be used without departing from the present disclosure. Tubing 908 may be mounted into extrusion pieces, which may be standardized or customized, in embodiments of the present disclosure. The system can disinfect a mass transit vehicle in as little as 25 seconds and the use of the small droplet provided by the spray/fogging system obviates the need for wipe down of surface after disinfection.

Disinfection system 902 may include a pump motor 909 that may be 12-volt and 6.8 amps for pumping within large mass transit vehicle 904. It should be appreciated that other voltages and/or currents may be utilized in embodiments of the present disclosure. For example, if a disinfection system is being used on surfaces within a room, a 110-volt pump motor may be used.

A controller/timer 112 may be used in disinfection system 902, and in an embodiment of the present disclosure, the controller/timer 112 may be 12-volt with multi-level timer settings. However, other voltages or types of settings may be used without departing from the present disclosure.

Connections utilized as part of disinfection system 902 may be UL-approved copper, 14-gauge wire with a jacket rubber sleeve, and the connections may be a crimp style with a terminal to each component of disinfection system 902 in an embodiment of the present disclosure. However, other types of connections (i.e., type and/or gauge of wire) may be used without departing from the present disclosure.

Disinfectant tank 910 may store a botanical component that may be delivered through tubing 908 to nozzles 906 using a 5-gallon aircraft aluminum tank in one embodiment of the present disclosure. The tank 910 would include an easy access opening 914 to enable ease of refill of the tank with the botanical component. It should be realized by one skilled in the art that other types of disinfectants could be utilized. The tubing 908 in one embodiment may comprise ¼ inch durable light weight poly tubing. The tubing 908 can be located in the lighting bar 911 of the mass transit vehicle 904 to conceal the tubing. The disinfectant tank 910 may be a 5-gallon fluid tank; however, other sizes may be utilized without departing from the present disclosure. Further, in an embodiment of the present disclosure, disinfectant tank 910 may be mounted under a seat on the driver's side of large mass transit vehicle 904 or any other seat of the mass transit vehicle 904 as shown in FIG. 9A. However, it should be appreciated that disinfectant tank 910 may be mounted or placed in other areas within large mass transit vehicle 904 without departing from the present disclosure. In yet a further embodiment, the disinfectant tank 910 may be mounted to the underside of a mass transit vehicle 902 or somewhere else externally if locations on the interior of the mass transit vehicle are not available.

The disinfection system 902 may sit within a holding tray 916 that contains the disinfectant tank 910, controller/timer 912 and the pump 904. The holding tray 916 would comprise a rectangular platform that held these components and had side panels 918 thereon. Slide-out rails 920 are included on each side of the holding tray 916 and in one embodiment connect with the side panels 918. The slide-out rails 920 enable the holding tray 916 to lateral slide out from under a seat or other enclosed area of the mass transit vehicle 902 to enable the disinfectant tank to be refilled or the controller/timer 912 and pump 909 mechanisms to be accessed and serviced.

Further, while the above system has been described as being installed within the interior of a mass transit vehicle. The disinfection system can be used with any enclosed area that there is a need for frequent disinfection due to high traffic or high-risk use such as a building or hallway.

Figure 10:
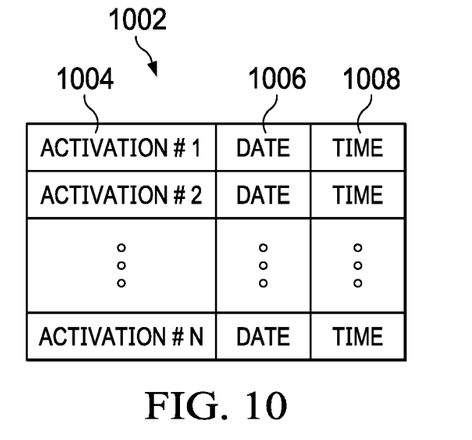
FIG. 10 illustrates a database for storing audit data of the disinfection system.

As referenced previously, each actuation of the disinfection system 902 may be logged within a memory 118 to enable the information to be downloaded to an external auditing party utilizing download interface 120. In this manner, the system can provide data describing each and every time a particular vehicle has been disinfected. Referring now to FIG. 10, there is illustrated one embodiment of the manner in which information relating to system activations may be saved within the memory 118 for downloading at a later point in time. The information may be stored within a database 1002. The database 1002 includes a plurality of data fields that store particular types of information about a particular activation of the disinfection system. The embodiment of FIG. 10 illustrates only one potential grouping of types of data fields and fewer, additional or various other types of information may be stored within the database and associated with each system activation. An activation identifier field 1004 would include some type of identifier that identified a particular application that occurred with respect to the disinfection system. The date field 1006 would include a month/day/year indicator that identified a particular day in which an activation of the system occurred. The time field 1008 provides an indication of the time of day at which a particular activation occurred in standard or military time. Additional data fields which could be utilized including indication of a fluid level of the botanical component within the storage unit 104, a length of time the system was active and spraying/fogging a mass transit vehicle and an indication of amount of botanical component utilized in a particular system activation. The database 1002 could also store GPS data from a GPS system associated with the disinfection system.

Figure 11:
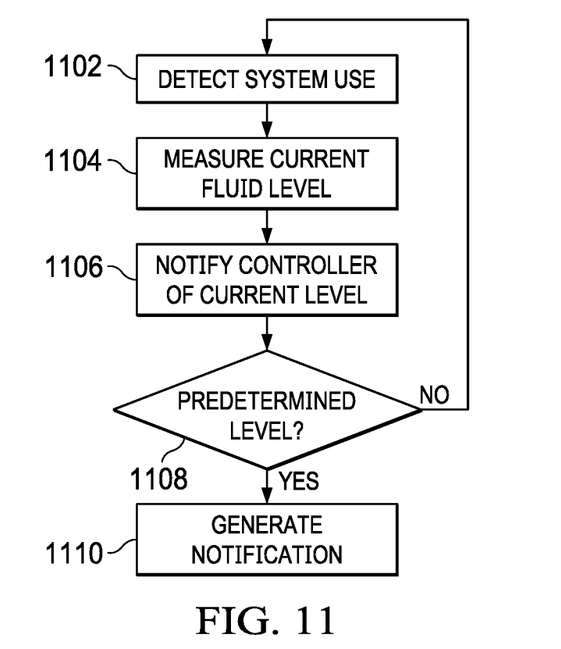
FIG. 11 illustrates a flow diagram of the process for monitoring a fluid level within a storage tank of the disinfection system.

Referring now to FIG. 11, there is provided a flow diagram of the process for detecting fluid level within the storage unit 104 using the level monitor 117. The controller detects a use by the system of the botanical component within the storage unit 104 to sanitize an area of a mass transit vehicle at step 1102. The level monitor 117 measures the current fluid level within the storage unit 104 at step 1104. The detected fluid level is provided to the controller 110 at step 1106. Within the controller 110, inquiry step 1108 determines if the current fluid level has reached a predetermined level within the storage unit 104. This predetermined level would be a fluid level low enough indicating that the system was about to run out of the botanical component. If inquiry step 1108 determines that the predetermined fluid level has not been reached, control passes back to step 1102 until the controller 110 next detects a system use. If inquiry step 1108 determines that the predetermined fluid level has been reached within the storage unit 104, the controller 110 generates a notification at step 1110 that provides an indication that the system level is low using a system indicator 119. The indicator 119 may comprise flashing LEDs, an audible alarm or any other means of providing an indication to an individual. An individual may then refill the storage unit 104 with additional botanical component responsive to this low-level indication.

Figure 12:
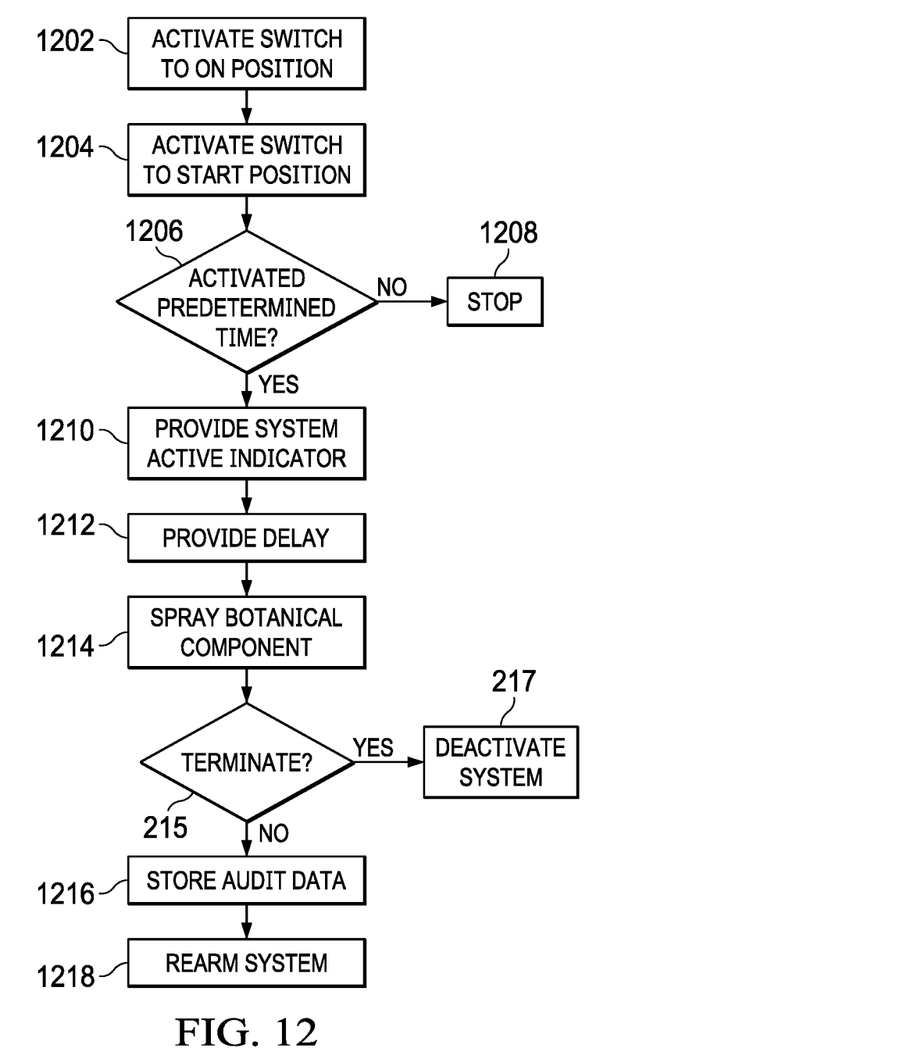
FIG. 12 illustrates a flow diagram of the process for actuating and operating the disinfection system.

Referring now to FIG. 12, there is illustrated the manner for actuation of the disinfection system. Initially at step 1202, the controller 110 determines that a switch 114 has been actuated to the on position to turn on the disinfection system. Next, the controller 110 determines at step 1204 that the switch 114 has been actuated to a start position. If inquiry step 1206 determines that the switch has not been activated to start position for a predetermined period of time, the process is stopped at step 1208 and no system initiation occurs. If inquiry step 1206 determines that the switch has been actuated to the start position for a predetermined period of time, this initiates the operation of the disinfection system. A system active indicator using the indicators 119 is provided at step 1210 via flashing lights or an audible indication. The system active indicator is provided for a predetermined time delay at step 1212 such that the individual who activated the system within the mass transit vehicle may exit the vehicle prior to disinfection of the mass transit vehicle interior. After the delay, the botanical component is sprayed within the interior of the mass transit vehicle at step 1214 for a predetermined period of time. The predetermined period of time that the nozzles spray the botanical component is configurable by the user. After the system has been activated, inquiry step 215 determines if the switch 114 is actuated to terminate system operation. If inquiry step 215 detects a system operation termination, the system is deactivated at step 217. This can stop operation of the system if someone accidentally gets caught inside the vehicle or disinfection area. In a preferred embodiment, the botanical component is sprayed within the interior of the mass transit vehicle for approximately 25 seconds (user configurable). Once the predetermined period of time has expired, the audit data associated with the system activation is stored at step 1216. This will include the identifier of the recent activation and associated time/date and any other relevant audit information that is needed. The disinfection system is then rearmed at step 1218 to be ready for a next activation to disinfect the mass transit vehicle.

It will be appreciated by those skilled in the art having the benefit of this disclosure that this disinfection system for mass transit vehicles provides an improved manner for quickly and inexpensively disinfecting the interior of a mass transit vehicle. It should be understood that the drawings and detailed description herein are to be regarded in an illustrative rather than a restrictive manner and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A system for disinfecting a mass transit vehicle, comprising:

a storage tank for storing a disinfection solution;

a plurality of nozzles installed in an interior of the mass transit vehicle, the plurality of nozzles projecting droplets of the disinfection solution into the interior of the mass transit vehicle when the system is activated;

a pump for pumping the disinfection solution from the storage tank to the plurality of nozzles on the interior of the mass transit vehicle;

a control switch for initiating operation of the system;

a system indicator for indicating an operational status of the system;

a controller for controlling the operation of the pump responsive to an input from the control switch;

wherein responsive to actuation of the control switch to a first position the controller actuates the system indicator for a first predetermined period of time and actuates the pump to pump the disinfection solution from the storage tank to the plurality of nozzles on the interior of the mass transit vehicle for a second predetermined period of time after expiration of the first predetermined period of time.

2. The system of claim 1 further including:

a memory connected to the controller containing a database for storing an indication of each actuation of the system and an associated time and date associated with the actuation; and wherein the controller stores the indication of each of the actuation of the system and the associated time and date of the actuation responsive to expiration of the second predetermined period of time.

3. The system of claim 1 further including:

a platform for containing the storage tank and the pump; and sliding rails connected to opposite sides of the platform to enable the platform to move between a first position and a second position.

4. The system of claim 1 further including:

a level monitor for monitoring a level of disinfection solution within the storage tank; and wherein responsive to expiration of the second predetermined period of time, the controller checks the level of disinfection solution within the storage tank using the level monitor and activates the system indicator responsive to a determination that the level of disinfection solution has reached a predetermined level.

5. The system of claim 1, wherein each of the plurality of nozzles further comprises:

a spray nozzle assembly for connecting a nozzle to a supply of the disinfection solution from the storage tank at a second end thereof and projecting the droplets of the disinfection solution from a first end thereof;

a holder base having a first end and a second end defining a first channel therein for receiving the first end of the spray nozzle assembly through the second end of the holder base, the holder base further defining a threaded channel at the first end thereof;

a holder base cap that connects to the second end of the holder base to secure the spray nozzle assembly within the holder base;

a holder trim cap having a disk-shaped portion having a first side and a second side and a threaded member portion extending from the second side of the disk-shaped portion of the holder trim cap, the holder trim cap further defining a second channel through the threaded member portion and the disk-shaped portion to enable the first end of the spray nozzle assembly to pass therethrough; and wherein the threaded member portion of the holder trim cap threadedly engages the threaded channel of the holder base to secure a structure of the mass transit vehicle between the first end of the holder base and the second side of the disk-shaped portion of the holder trim cap to securely position the nozzle within the mass transit vehicle.

6. The system of claim 5, wherein the holder base and the holder base cap further define a third channel perpendicular to the first channel within the holder base when connected, the third channel securing the spray nozzle assembly within the connected holder base and holder base cap.

7. The system of claim 5, wherein the holder base and the holder base cap further define a pair of threaded holes for receiving a pair of connectors for securing the holder base to the holder base cap.

8. The system of claim 1, wherein the plurality of nozzles further project the droplets in up to a 120 degree coverage area.

9. A system for disinfecting a mass transit vehicle, comprising:
a storage tank for storing a disinfection solution;
a plurality of nozzles installed in an interior of the mass transit vehicle, the plurality of nozzles projecting droplets of the disinfection solution into the interior of the mass transit vehicle when the system is activated, wherein each of the plurality of nozzles further comprises:
a spray nozzle assembly for connecting a nozzle to a supply of the disinfection solution from the storage tank at a second end thereof and projecting the droplets of the disinfection solution from a first end thereof;
a holder base having a first end and a second end defining a first channel therein for receiving the first end of the spray nozzle assembly through the second end of the holder base, the holder base further defining a threaded channel at the first end thereof;
a holder base cap that connects to the second end of the holder base to secure the spray nozzle assembly within the holder base;
a holder trim cap having a disk-shaped portion having a first side and a second side and a threaded member portion extending from the second side of the disk-shaped portion of the holder trim cap, the holder trim cap further defining a second channel through the threaded member portion and the disk-shaped portion to enable the first end of the spray nozzle assembly to pass therethrough; and
wherein the threaded member portion of the holder trim cap threadedly engages the threaded channel of the holder base to secure a structure of the mass transit vehicle between the first end of the holder base and the second side of the disk-shaped portion of the holder trim cap to securely position the nozzle within the mass transit vehicle;
a pump for pumping the disinfection solution from the storage tank to the plurality of nozzles on the interior of the mass transit vehicle;
a control switch for initiating operation of the system;
a system indicator for indicating an operational status of the system;
a controller for controlling the operation of the pump responsive to an input from the control switch; and
wherein responsive to actuation of the control switch to a first position the controller actuates the system indicator for a first predetermined period of time and actuates the pump to pump the disinfection solution from the storage tank to the plurality of nozzles on the interior of the mass transit vehicle for a second predetermined period of time after expiration of the first predetermined period of time.

10. The system of claim 9 further including:
a memory connected to the controller containing a database for storing an indication of each actuation of the system and an associated time and date associated with the actuation; and
wherein the controller stores the indication of each of the actuation of the system and the associated time and date of the actuation within the memory responsive to expiration of the second predetermined period of time.

11. The system of claim 9 further including:
a platform for containing the storage tank and the pump; and
sliding rails connected to opposite sides of the platform to enable the platform to move between a first position and a second position.

12. The system of claim 9 further including:
a level monitor for monitoring a level of disinfection solution within the storage tank; and
wherein responsive to expiration of the second predetermined period of time, the controller checks the level of disinfection solution within the storage tank using the level monitor and activates the system indicator responsive to a determination that the level of disinfection solution has reached a predetermined level.

13. The system of claim 12, wherein the holder base and the holder base cap further define a third channel perpendicular to the first channel within the holder base when connected, the third channel securing the spray nozzle assembly within the connected holder base and holder base cap.

14. The system of claim 12, wherein the holder base and the holder base cap further define a pair of threaded holes for receiving a pair of connectors for securing the holder base to the holder base cap.

15. The system of claim 9, wherein the plurality of nozzles further project the droplets in an 85 degree coverage area.

16. A system for disinfecting a mass transit vehicle, comprising:
a storage tank for storing a disinfection solution;
a plurality of nozzles installed in an interior of the mass transit vehicle, the plurality of nozzles projecting droplets of the disinfection solution into the interior of the mass transit vehicle when the system is activated;
a pump for pumping the disinfection solution from the storage tank to the plurality of nozzles on the interior of the mass transit vehicle;
a control switch for initiating operation of the system;
a system indicator for indicating an operational status of the system;
a controller for controlling the operation of the pump responsive to an input from the control switch;
memory connected to the controller containing a database for storing an indication of each actuation of the system and an associated time and date associated with the actuation;
wherein responsive to actuation of the control switch to a first position the controller actuates the system indicator for a first predetermined period of time and actuates the pump to pump the disinfection solution from the storage tank to the plurality of nozzles on the interior of the mass transit vehicle for a second predetermined period of time after expiration of the first predetermined period of time; and wherein the controller stores the indication of each of the actuation of the system and the associated time and date of the actuation within the memory responsive to expiration of the second predetermined period of time.

17. The system of claim 16 further including:
a platform for containing the storage tank and the pump; and
sliding rails connected to opposite sides of the platform to enable the platform to move between a first position and a second position.

18. The system of claim 16 further including:
a level monitor for monitoring a level of disinfection solution within the storage tank; and
wherein responsive to expiration of the second predetermined period of time, the controller checks the level of disinfection solution within the storage tank using the level monitor and activates the system indicator responsive to a determination that the level of disinfection solution has reached a predetermined level.

19. The system of claim 16, wherein each of the plurality of nozzles further comprises:
a spray nozzle assembly for connecting a nozzle to a supply of the disinfection solution from the storage tank and projecting the droplets of the disinfection solution;
a holder base having a first end and a second end defining a first channel therein for receiving the spray nozzle assembly through the second end of the holder base, the holder base further defining a threaded channel at the first end thereof;
a holder base cap that connects to the second end of the holder base to secure the spray nozzle assembly within the holder base;
a holder trim cap having a disk-shaped portion having a first side and a second side and a threaded member portion extending from the second side of the disk-shaped portion of the holder trim cap, the holder trim cap further defining a second channel through the threaded member portion and the disk-shaped portion to enable the spray nozzle assembly to pass therethrough;
wherein the threaded member portion of the holder trim cap threadedly engages the threaded channel of the holder base to secure a structure of the mass transit vehicle between the first end of the holder base and the second side of the disk-shaped portion of the holder trim cap to securely position the nozzle within the mass transit vehicle; and
wherein the holder base and the holder base cap further define a third channel perpendicular to the first channel within the holder base when connected, the third channel securing the spray nozzle assembly within the connected holder base and holder base cap.

* * * * *